United States Patent [19]
Hazony et al.

[11] Patent Number: 5,176,034
[45] Date of Patent: Jan. 5, 1993

[54] ULTRASONIC TRANSDUCER

[75] Inventors: Dov Hazony, University Heights; Richard E. Berris, Jr., Chagrin Falls, both of Ohio

[73] Assignee: J. W. Harley Inc., Twinsburg, Ohio

[21] Appl. No.: 702,884

[22] Filed: May 20, 1991

Related U.S. Application Data

[63] Continuation-in-part of Ser. No. 490,824, Mar. 7, 1990, Pat. No. 5,016,474, which is a continuation-in-part of Ser. No. 219,076, Jul. 14, 1988, Pat. No. 4,907,454, which is a continuation-in-part of Ser. No. 25,943, Mar. 16, 1987, Pat. No. 4,757,713, which is a continuation-in-part of Ser. No. 702,926, Feb. 19, 1985, Pat. No. 4,649,749.

[51] Int. Cl.[5] .............................................. G01N 29/00
[52] U.S. Cl. ..................................... 73/597; 73/632
[58] Field of Search ................. 73/587, 589, 597, 598, 73/604, 632, 644; 310/336, 338

[56] References Cited

U.S. PATENT DOCUMENTS

| | | | |
|---|---|---|---|
| 4,272,924 | 6/1981 | Masuko et al. | 73/597 |
| 4,437,332 | 3/1984 | Pittaro | 73/644 |
| 4,510,793 | 4/1985 | Ploegaert et al. | 73/597 |
| 4,922,754 | 5/1990 | Horne et al. | 63/644 |

Primary Examiner—Louis Arana
Attorney, Agent, or Firm—James A. Hudak

[57] ABSTRACT

An ultrasonic piezoelectric transducer and a method for measuring and/or monitoring various physical properties of a member, in-situ, are disclosed. The transducer includes a sleeve which is received in a blind bore provided in the member, a piezoelectric element positioned within the blind bore, and an aligning spacer means interposed between the end of the sleeve and the piezoelectric element. By the application of appropriate voltage pulses to the piezoelectric element causing interrogating signals to be applied to the member, and the measurement of the time interval between the application of an interrogating signal and the receipt of a return signal from the member, various physical properties of the member and structural information regarding same can be determined.

12 Claims, 5 Drawing Sheets

_Fig. 8_

_Fig. 9_

_Fig. 10_

_Fig. 11_

_Fig. 12_

_Fig. 13_

ULTRASONIC TRANSDUCER

This application is a continuation-in-part of Ser. No. 07/490,824 filed Mar. 7, 1990 now U.S. Pat. No. 5,016,474 which is a continuation-in-part of Ser. No. 07/219,076 filed Jul. 14, 1988 now U.S. Pat. No. 4,907,454 which is a continuation-in-part of Ser. No. 07/025,943 filed Mar. 16, 1987 now U.S. Pat. No. 4,757,713 which is a continuation-in-part of Ser. No. 06/702,926 filed Feb. 19, 1985 now U.S. Pat. No. 4,649,749.

TECHNICAL FIELD

The present invention relates to a method for measuring and/or monitoring the amount of material which has been removed from a member through wear, machining, etc., and more particularly to an ultrasonic piezoelectric transducer for measuring and/or monitoring the amount of material which has been removed from a member and other physical properties of the member in-situ, or alternatively for measuring the position of a surface on or in proximity to the member.

BACKGROUND ART

Various approaches have been devised for detecting, monitoring and measuring the amount of wear which has occurred to a wear member. For example, in the area of rotating equipment, a number of electrical devices are available to detect and monitor bearing wear. These devices are based upon a number of detection techniques. Thus, wear detection might depend upon the completion of an electrical circuit through the bearing when there is excessive bearing wear, or it might depend upon the generation of a voltage if the shaft rotates eccentrically, or it might depend upon the detection of an abnormal temperature rise of the bearing. Each of these approaches has some inherent disadvantages with respect to accuracy and does not measure actual bearing wear, bearing wall thickness or the amount of material which has been removed from the bearing, i.e., each approach is responsive to bearing wear but does not measure quantitatively the amount of wear that has occurred, the wall thickness remaining or the amount of material which has been removed.

Other approaches have been devised to measure the thickness of a workpiece or wear member, and by measuring such thickness, the amount of wear which has occurred can be calculated. These approaches have numerous commercial and/or industrial applications, however, their use for measuring the thickness of or wear which has occurred to a work surface in-situ is cost prohibitive. In addition, these approaches typically utilize devices fabricated from materials which limit their applications to an operating environment having a temperature of normally less than 75° C., and cause the resulting readings to be dependent upon the temperature of the operating environment. It has also been found that the materials utilized for these devices cannot withstand severe operating environments which further limits the applications in which they can be used. Thus, these devices and measurement techniques are not usable for measuring and/or monitoring the thickness of or wear which has occurred to work surfaces, such as a sleeve bearing, in an elevated temperature operating environment such as might exist in rotating equipment. This inability to measure and/or monitor wear in-situ can result in costly machine downtime to inspect the condition of the bearings. Alternatively, this inability can result in unnecessary damage to the rotating equipment due to bearing failure which was not promptly detected.

Because of the foregoing, it has become desirable to develop a device which can be utilized to measure and/or monitor in-situ the thickness of, the amount of wear which has occurred to, and the amount of material which has been removed from a member such as sleeve or thrust bearings, brake discs or pads, clutch plates and sealing members. Ideally, the resulting device could also be used for measuring other physical properties (such as temperature or pressure) of the member, in-situ, and positional properties of the member relative to other members or surfaces defining same.

SUMMARY OF THE INVENTION

The present invention provides an ultrasonic piezoelectric transducer that can be mounted within the wall of a wear member, such as a sleeve or thrust bearing, brake disc or pad, clutch plate or sealing device, so that measurements of wall thickness, the amount of material which has been removed through wear, and other physical properties such as temperature and/or pressure, can be made in-situ. The transducer, which is an integral part of the member in which it is mounted, includes an outer sleeve which is threadedly received in a blind bore within the wear member, a piezoelectric element which is positioned within the blind bore, and spacer means interposed between the end of the outer sleeve and the piezoelectric element. The spacer means and the end of the outer sleeve have complementary configurations permitting the spacer means to align itself within the end of the outer sleeve and apply a substantially uniform compressive force to the piezoelectric element. The application of such a substantially uniform compressive force causes a firm, electrical and acoustical contact to be formed between the piezoelectric element and the bottom of the blind bore which insures a highly accurate measurement of the wall thickness between the bottom of the blind bore and the inner surface of the wear member. For example, it has been found experimentally that this transducer can readily measure the wall thickness of and/or the amount of material which has been removed from the wall of a bronze bearing at temperatures over 300° F. with a repeatability in the submicron range utilizing state-of-the-art electronics. The transducers can also be located in a predetermined arrangement around the periphery of the wear member so that wear and/or material removed can be measured and/or monitored around the periphery thereof. In addition, it has been found that other physical properties such as strain resulting from stress being applied to the wear member can be monitored with the transducer. It has also been found that the transducer can be utilized to determine local temperatures within the wear member and, in the case of rotating machinery, the relative vibration and alignment between the shaft and the member can be measured and/or monitored with the transducer. Alternatively, the position of the shaft relative to a wear surface can be determined, i.e., the oil film between the wear surface and the outer periphery of the shaft can be "jumped" to determine the position of the shaft. It has been further found that if ball bearings are being utilized, each ball exhibits specific pressure characteristics which change due to wear or fracture, and that these pressure characteristics can be measured and/or monitored with the transducer.

In an alternate embodiment of the invention, a mounting ring is provided to position one or more transducers against the outer surface of the wear member. In this embodiment, the piezoelectric elements contact the outer surface of the wear member and the total thickness of the wear member is measured.

In still another alternate embodiment of the invention, the blind bores within the wear member are replaced with though bores to reduce production costs. A transducer assembly is received within each of the through bores so that its end is flush with the inner surface of the wear member. In this embodiment, the end of the transducer assembly is actually an integral part of the wear surface and the thickness of the end of the transducer assembly is being measured.

Regardless of the embodiment utilized, a separate transducer may be placed in the same environment as the other transducers to provide a relative time reference or a plurality of relative time references for temperature compensation. Several embodiments of relative time references are disclosed.

DESCRIPTION OF THE PREFERRED EMBODIMENT

Figure 1:
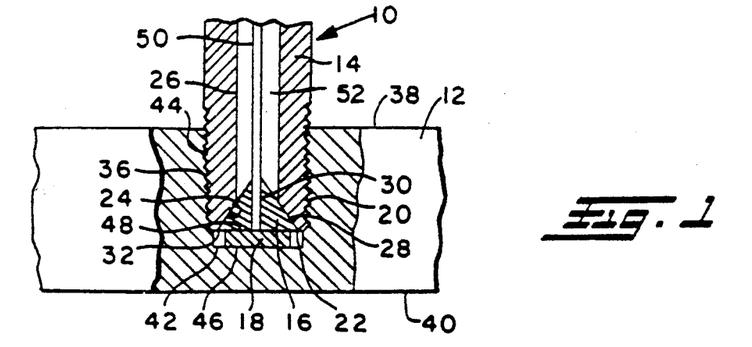
FIG. 1 is a partial cross-sectional view of an ultrasonic piezoelectric transducer embodying the invention of this disclosure and installed in a wear member.

Referring now to the drawings where the illustrations are for the purpose of describing the preferred embodiment of the present invention and are not intended to limit the invention hereto, FIG. 1 is a cross-sectional view of the transducer 10 installed in a wear member 12, such as a sleeve or thrust bearing, clutch plate, brake disc or pad, sealing member, valve or the like, in order to measure and/or monitor the thickness of, the amount of wear which has occurred to, and the amount of material which has been removed from the wear member. The transducer 10 is comprised of an outer sleeve 14, an aligning and electrically insulating spacer 16 received within the end of the outer sleeve, and a piezoelectric element 18.

The outer sleeve 14 is typically fabricated from round tubing, such as brass tubing or the like, which has threads 20 formed adjacent to one end thereof. Typically, the tubing material has the same or similar thermal expansion properties as that of the wear member 12 to maintain a firm contact therewith. This firm contact is provided by the threads 20 which engage complementary threads provided in the wear member 12, as hereinafter described. The threads 20 also permit the adjustment of the outer sleeve 14 within the wear member 12 to optimize the operation of the transducer 10 as discussed later. It should be noted that other approaches are possible for the adjustable attachment of the outer sleeve 14 to the wear member 12, such as a bracket arrangement (not shown) that is adjustable with respect to the wear member 12 and which retains the sleeve 14. The end 22 of the outer sleeve 14 has an indentation provided therein forming a surface 24 connecting the end 22 of the sleeve 14 with the inner circumferential wall 26 of the sleeve. This indentation may have a curved configuration, such as semispherical or parabolic, or it may have a conical configuration which is preferred to permit alignment of the spacer 16 therein.

The aligning and electrically insulating spacer 16 is fabricated from a ceramic or ceramic-like material that is capable of sustaining high temperatures and high pressures. For example, pyrolytic boron nitride or another ceramic-like material can be used for the spacer 16. The particular ceramic or ceramic like-material utilized for the spacer 16 is selected to properly compensate for the thermal expansion properties of the other components comprising the transducer 10 and the wear member 12 so that the spacer 16 will maintain a substantially uniform compressive force on the piezoelectric element 18 over a broad operating temperature range. The spacer 16 typically has a conical configuration that is complementary to that of the indentation formed in the end 22 of the outer sleeve 14. The spacer 16 is received within the indentation so that the outer surface 28 defining its conical configuration contacts the surface 24 formed by the indentation. The use of conical surfaces 24, 28 formed on the outer sleeve 14 and the spacer 16, respectively permits the alignment of the spacer 16 within the outer sleeve 14 through elastic deformation of the spacer 16 and the indentation formed in the end 22 of the outer sleeve 14. In contrast, self-alignment of the spacer 16 within the outer sleeve 14 can be achieved by using a semi-spherical or parabolic configuration for the surfaces 24, 28 formed on the end 22 of the outer sleeve 14 and the spacer 16, respectively. It should be noted that regardless of the shape of the complementary configurations used for the spacer 16 and the indentation in the end 22 of the outer sleeve 14, a precise fit of the spacer 16 within the indentation is not necessary since any variations in size or shape will be compensated for by the elastic deformation of the spacer 16 and the indentation and/or by the self-alignment of the complementary curved surfaces. The alignment of the spacer 16 within the outer sleeve 14, whether by elastic deformation of the spacer 16 and the indentation in the end 22 of the outer sleeve 14 or by self-alignment through complementary curved surfaces, is necessary to ensure the application of a uniform compressive force on the piezoelectric element 18. Such a substantially uniform compressive force also minimizes the possibility of damaging the piezoelectric element 18 through the application of a nonuniform compressive force thereto. Even though both of the foregoing approaches apply a substantially uniform compressive force to the piezoelectric element 18, it has been found that the use of an appropriate conical configuration for the spacer 16 and the indentation in the end 22 of the outer sleeve 14 is easier to implement and may result in a substantially higher absorption and obliteration of spurious echoes from the primary ultrasonic signal than if complementary curved configurations are used for the spacer 16 and the indentation in the end 22 of the outer sleeve 14. Thus, the use of a conical configuration for the spacer 16 and the end 22 of the outer sleeve 14 generally results in a higher signal to noise ratio than if complementary curved configurations are used for same. In summary, the spacer 16 is necessary in this structure in order to provide a substantially uniform compressive force to the piezoelectric element 18 and to absorb and obliterate spurious echoes. Regardless of the configuration utilized for the spacer 16, an aperture 30 is formed therethrough. This aperture is sufficiently large to permit the passage of an electric conductor therethrough.

The wear member 12 is provided with a blind bore 36 therein. The blind bore 36 is located so as to be substantially perpendicular to the outer and inner surfaces 38, 40, respectively of the member 12. If the member 12 is a sleeve bearing, the blind bore 36 is directed radially inwardly so as to be normal to the inner surface 40 of the member 12. The blind bore 36 is of a predetermined depth and has a substantially flat surface 42 at the bottom thereof. The distance between the flat surface 42 and the inner surface 40 of the member 12 is the distance to be measured and/or monitored. The blind bore 35 may also have threads 44 formed therein which terminate adjacent to the bottom thereof.

The piezoelectric element 18 is a standard state-of-the-art device and typically has a round disc-like shape. The element 18 can be formed from commercially available piezoelectric transducer material, such as PZT-5H available from Vernitron, Inc. of Bedford, Ohio. The size of the element 18 is a function of the overall size of the transducer 10, however, an element having a diameter of 0.080 inch and a thickness of 0.003 inch has been tested experimentally with excellent results. The diameter of the element 18 is slightly less than the diameter of the blind bore 36 provided in the wear member 12. The element 18 is responsive to a short voltage pulse, such as a 200 volt DC pulse of 10 nanosecond duration, and converts the voltage pulse into a pressure pulse (often referred to as a "stress pulse") which is applied to the surface of the material whose thickness is to be measured and/or monitored. Similarly, the piezoelectric element 18 converts the "echo" return pressure pulse from the opposite surface of the material whose thickness is being monitored into a voltage pulse for measurement purposes. The substantially uniform compressive force applied to the piezoelectric element 18 by the spacer 16 ensures that the element 18 is firmly "seated" within the blind bore 36 for the proper transmission of the voltage pulse into the element 18 and the reception of the reflected "echo" pulse by the element.

In order to assemble the transducer 10, the piezoelectric element 18 is received within the blind bore 36 and positioned so that one side 46 thereof contacts the flat surface 42 at the bottom of the blind bore 36. Inasmuch as the diameter of the element 18 is only slightly less than the diameter of the blind bore 36, the center of the element 18 and the center of the flat surface 42 at the bottom of the blind bore 36 will substantially coincide, however, such coincidence is not necessary for the proper operation of the transducer 10. The other side 48 of the piezoelectric element 18 may be electrically connected to an electrical conductor 50. The electrical conductor 50 is received through the aperture 30 provided in the spacer 16, and the spacer 16 is received in the blind bore 36 so that its base 32 contacts the side 48 of the piezoelectric element 18 which is mechanically and electrically connected to the electrical conductor 50. The threads 20 on the outer sleeve 24 are coated with an adhesive, such as Loctite, and the sleeve 14 is threadedly advanced into the wear member 12 until the conical surface 24 provided on its end 22 engages the outer surface 28 of the spacer 16. Further advancement of the outer sleeve 14 into the wear member 12 causes the elastic deformation of the spacer 16 and the indentation in the end 22 of the outer sleeve 14, and the application of a substantially uniform compressive force by the base 32 of the spacer 16 to the side 48 of the piezoelectric element 18. If complementary curved configurations, such as semispherical or parabolic, are used for the spacer 16 and the indentation in the end 22 of the outer sleeve 14, the spacer 16 will self-align itself within the indentation in the end 22 of the outer sleeve 14 so that its base 32 will apply a substantially uniform compressive force to the side 48 of the piezoelectric element 18. Regardless of the shape of the spacer 16 and the indentation in the end 22 of the outer sleeve 14, the outer sleeve 14 is threadedly advanced into the wear member 12 by manually rotating the outer sleeve 14 until a snug fit exists between the indentation provided in its end 22 and the outer surface 28 of the spacer 16, and between the base 32 of the spacer 16 and the side 48 of the piezoelectric element 18. In order to ensure that such a snug fit exists, the foregoing advancement of the outer sleeve 14 into the wear member 12 is monitored by a pulser-receiver device and an oscilloscope (all not shown). With this apparatus a sequence of short voltage pulses is applied by the pulser to the transducer 10 while the outer sleeve 14 is being threadedly advanced into the wear member 12 so that the sleeve 14 can be rotationally adjusted until the optimum return "echo" pulse, shown on the oscilloscope, is recorded by the receiver. In this manner, a snug fit between the foregoing components is assured and the transducer 10 and the wear member 12 are "matched" to provide the optimum return "echo" pulse with respect to shape, amplitude and signal to noise ratio. This snug fit is retained through the use of the aforementioned adhesive, such as Loctite, on the threads of the outer sleeve 14, thus preventing any further movement of the outer sleeve 14 with respect to the wear member 12. In essence, the transducer 10 becomes permanently affixed to and an integral part of the wear member 12, and the snug fit between the indentation in the end 22 of the outer sleeve 14 and the outer surface 28 of the spacer 16 is maintained throughout the life of the device.

Since the piezoelectric element 18 is somewhat deformable under a compressive force, the application of a substantially uniform compressive force thereto results in a firm, optimum electrical and acoustical contact between the side 46 of the element 18 and the flat surface 42 at the bottom of the blind bore 36. By providing such a firm, optimum electrical and acoustical contact with the flat surface 42 of the blind bore 36, any signals emanating from the piezoelectric element 18 will be properly directed toward the inner surface 40 of the wear member 12 to be measured and/or monitored, and the wear member 12 will provide the proper electrical ground for the system. Thus, the surfaces 24, 28 compensate for deviations in manufacturing tolerances in the components involved, and the possibility that the blind bore 36 may not be positioned exactly normal to the inner surface 40 of the wear member 12. Both of these conditions could result in the piezoelectric element 18 not firmly contacting the flat surface 42 of the blind bore 36 which, in turn, could result in inaccurate measurements and/or system malfunctions. After the transducer 10 has been assembled and installed in the wear member 12, the area 52 enclosed by the inner circumferential wall 26 of the outer sleeve 14 and containing the electrical conductor 50 may be filled with a dense insulating and dampening material such as epoxy, e.g., Duro epoxy, loaded with tungsten for application temperatures less than 400° F. or loaded ceramic adhesive for temperatures in excess of 400° F. This electric insulation material and the spacer 16 preferably match the acoustical impedance of the piezoelectric element 18 and help suppress spurious echoes from interfering with the primary measurement.

Figure 2:
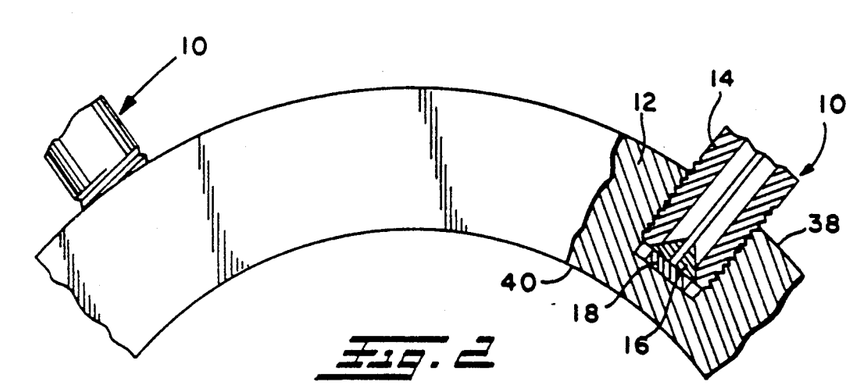
FIG. 2 is a partial cross-sectional view of a plurality of ultrasonic piezoelectric transducers embodying the invention of this disclosure and installed in and around the periphery of a wear member, such as a sleeve bearing.

The wear member 12 may have a configuration that is either flat, such as a brake disc, clutch plate, face type seal or thrust bearing, or circular, such as a sleeve bearing or ring type seal. In any case, a plurality of transducers can be utilized to measure and/or monitor wear at various locations on the wear member 12. If a sleeve bearing is utilized, the plurality of transducers 10 can be placed within the outer bearing wall and around the periphery of the bearing, as shown in FIG. 2. In this manner, the thickness of, the amount of wear which has occurred to, and the amount of material which has been removed from the bearing can be measured and/or monitored at various locations around the periphery thereof. Thus, by placing the transducer 10 within one or more blind bores 36 within the bearing, wear can be measured and/or monitored in situ, eliminating costly periodic machine downtime to inspect the condition of the bearing. Machine downtime would only occur when a transducer indicates that sufficient wear has occurred to justify the replacement of the bearing.

Figure 3:
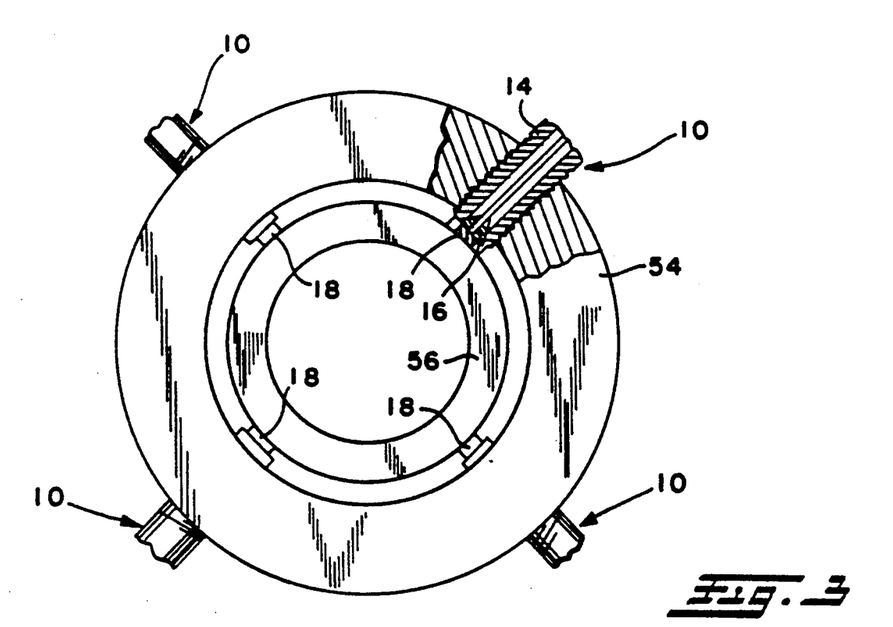
FIG. 3 is a partial cross-sectional view of a mounting ring for retaining one or more ultrasonic piezoelectric transducers against the outer surface of a wear member, such as a sleeve bearing or a ball bearing.

Alternatively, rather than placing a plurality of transducers 10 within the blind bores provided in the outer bearing wall, a mounting attachment 54, such as a ring as shown in FIG. 3, can be used to retain the transducers 10 in a radially spaced apart relationship. In such an arrangement, the mounting attachment 54 is slipped over the sleeve bearing 56 and the piezoelectric elements 18 firmly contact the outer surface of the bearing wall. Thus, no blind bores, which could damage the bearing or affect its performance, are required in the bearing wall. The foregoing is particularly important in the case of ball bearings. In the arrangement shown in FIG. 3, the radius of the curvature of the bearing 56 is substantially greater than the diameter of each piezoelectric element 18. Since a substantial compressive force is being applied to each element 18 by its associated spacer 16, it has been found that sufficient surface contact exists between each element 18 and the outer surface of the bearing 56 to produce very accurate distortionless measurements of wall thickness. Thus, by using this apparatus, the thickness of, the amount of wear which has occurred to, the rate of wear of, and the amount of material which has been removed from the bearing wall can be measured and/or monitored at various locations on the bearing. From the foregoing, it is apparent that the mounting attachment 54 can also be used to measure the wall thickness or the overall thickness of a non-wear cylindrical member, such as a machine member, by slipping the mounting attachment 54 over the non-wear member and positioning the piezoelectric elements 18 so that they firmly contact the outer surface of the non-wear member at specific locations thereon. Thus, the transducer 10 can be utilized for precision in-processing gauging or in-process measuring of strain.

In addition to being able to measure and/or monitor the thickness of, the amount of wear which has occurred to, and the amount of material which has been removed from a wear member in-situ, the construction of the transducer 10 provides another advantage in that no buffer element is required between the piezoelectric element 18 and the wall whose thickness is being measured and/or monitored, i.e., the distance between the flat surface 42 of the blind bore 36 and the inner surface 40 of the wear member 12. Typically, in prior art devices such a buffer element is required for mechanical support, impedance matching and sealing of the transducer, however, its use greatly attenuates and degrades the primary pulses produced by the transducer and the reflected "echo" pulses received by the transducer. Inasmuch as the transducer 10 requires no buffer element, such signal attenuation and degradation does not occur. In addition, because of the absence of a buffer element, a firm electrical and acoustical contact can be made by the piezoelectric element 18 directly to the wall whose thickness is being measured and/or monitored, and the resulting measurements have a much higher degree of accuracy than those resulting from prior art devices. For example, measurements with a repeatability in the submicron range utilizing state-of-the-art electronics have been achieved. And lastly, due to the inherent simplicity of the structure of the transducer, it is substantially less costly to produce than the prior art devices.

Figure 4:
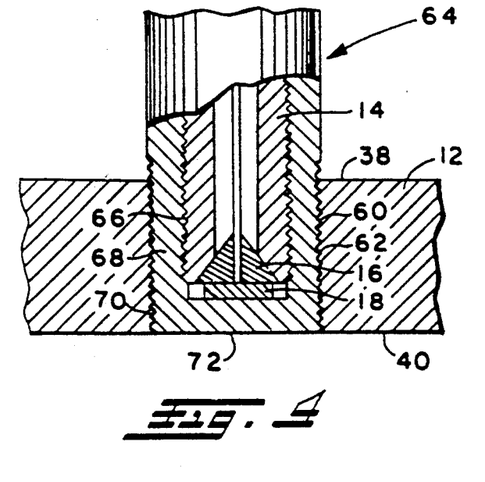
FIG. 4 is a partial cross-sectional view of an alternate embodiment of an ultrasonic piezoelectric transducer embodying the invention of this disclosure and installed in a wear member.

In an alternate embodiment of the invention, as shown in FIG. 4, the blind bore 36 in the wear member 12 is replaced with a through bore 60 connecting the outer and inner surfaces 38, 40 of the member 12. The through bore 60 may have threads 62 formed therein. A transducer 64 comprising an outer sleeve 14, a spacer 16, and a piezoelectric element 18 is received within a blind bore 66 in a wear reference member 68 which may have threads 70 formed on the outer surface thereof. The wear reference member 68 is received within the through bore 60 so that its end 72 is substantially flush with the inner surface 40 of the wear member 12. The inner surface 40 of the wear member 12 is then machined to ensure that the end 72 of the wear reference member 68 is flush with the inner surface 40. It should be noted that the material utilized for the wear reference member 68 is not critical inasmuch as only the thickness of the end of the reference member 68 is being monitored and/or measured. The operation of this embodiment is similar to the previous embodiment utilizing a blind bore, however, it is easier and less costly to produce.

Figure 5:
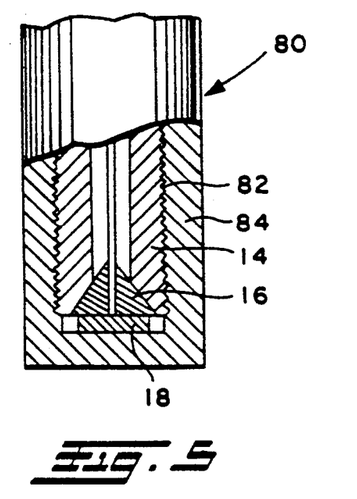
FIG. 5 is similar to FIG. 4 in that it is a partial cross-sectional view of an ultrasonic piezoelectric transducer which may provide a relative time reference for temperature compensation.

With any of the foregoing embodiments, it might be desired to compensate for the temperature and pressure of the environment and the strains existing on the transducer. Such compensation can be accomplished by using a transducer that provides a relative time reference, such as transducer 80, shown in FIG. 5. The structure of this transducer 80 is similar to transducer 10, in that it comprised of an outer sleeve 14, a spacer 16, and a piezoelectric element 18, however, the foregoing components are received in a blind bore 82 provided in a reference member 84, which is similar to wear reference member 68. The material utilized for the reference member 84 is the same as or similar to the material for the wear member 12 if a blind bore 36 is utilized in the member 12, or the same as or similar to the material for the wear reference member 68 if a through bore 60 is provided in the wear member 12. The assembly of the transducer 80 and the reference member 84 is placed within the same temperature, pressure or material environment as the other transducers 10, though not necessarily contacting the wear member 12. By monitoring the measurements of the reference distance, produced by the transducer 80, the measurements produced by the transducer 10 can be adjusted to compensate for possible measurement variations caused by operating environment changes.

Figure 6:
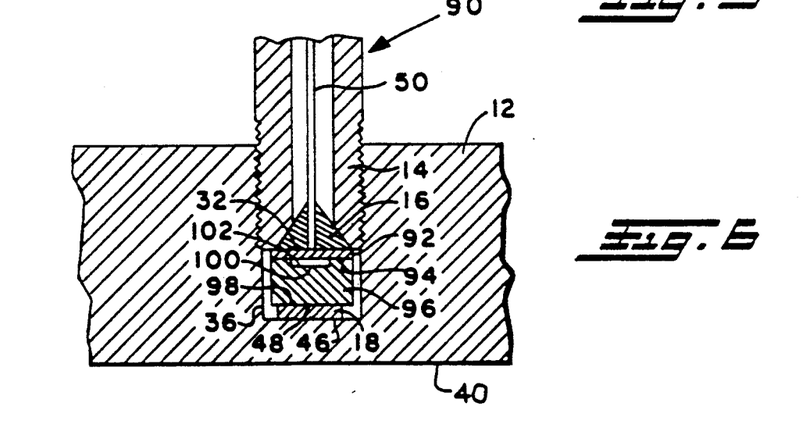
FIG. 6 is a partial cross-sectional view of another embodiment of an ultrasonic piezoelectric transducer installed in a wear member and which provides a relative time reference for temperature compensation.

Another embodiment of a transducer that provides a relative time reference is transducer 90 shown in FIG. 6. The structure of this transducer is similar to the transducer 80 in that it is comprised of an outer sleeve 14, a spacer 16, a piezoelectric element 18, and an electrical conductor 50, however, the foregoing components are received in a blind bore 36 provided in the wear member 12. The electrical conductor 50 is attached to a disc-shaped electrical connector 92 which is interposed between the base 32 of spacer 16 and the top surface 94 of a reference acoustical member 96 having a cylindrical configuration. The bottom surface 98 of the reference acoustical member 96 firmly contacts the other side 48 of the piezoelectric element 18. The diameters of the disc-shaped electrical connector 92 and the reference acoustical member 96 are similar and are slightly less than the diameter of the blind bore 36 permitting the easy insertion therein. The reference acoustical member 96 is formed from the same material as, or similar material to, the material comprising the wear member 12. A recess 100, which is preferably cylindrical in configuration, is provided in the top surface 94 of the reference acoustical member 96 and is concentric with the center of the reference member 96 leaving the area between the diameter of the recess 100 and the outer diameter of the reference member 96 in contact with the bottom surface of the electrical connector 92. A low impedance acoustical material 102 may be provided in the recess 100 or the recess 100 may be left empty in which case it would have approximately a zero impedance. The low impedance of the recess 100 provides a relatively large reflection coefficient for any pressure wave intercepted thereby. Such a relatively large reflection coefficient is beneficial for the operation of this transducer 90, hereinafter described.

Operationally, a short voltage pulse is applied to the piezoelectric element 18 via the electrical conductor 50, the electrical connector 92 and the reference acoustical member 96. The piezoelectric element 18 converts the voltage pulse into two pressure pulses (stress pulses) which are transmitted in opposite directions--one pressure pulse being transmitted into the wear member 12 via the one side 46 of the element 18 and the other pressure pulse being transmitted into the reference acoustical member 96 via the other side 48 of the element 18. The pressure pulse transmitted into the wear member 12 is reflected by the inner surface 40 of the wear member 12 back toward the one side 46 of the piezoelectric element 18 and is intercepted by same. Similarly, the pressure pulse transmitted into the reference acoustical member 96 is reflected by the low impedance acoustical material 102 in the recess 100 back toward the other side 48 of the piezoelectric element 18 and is intercepted by same. Inasmuch as the thickness of the reference acoustical member 96 varies independently of wear and is typically affected only by variations in temperature, the elapsed time between the transmission of the initial pressure pulse and the receipt of the "echo" return pressure pulse can be determined and utilized as a temperature reference parameter. Thus, in essence, one pressure pulse "monitors" the thickness of the wear member 12 and the other pressure pulse "monitors" the thickness of the reference acoustical member 96 between the top surface of the piezoelectric element 18 and the bottom of the recess 100 containing the low impedance material 102. By "measuring" the latter thickness through elapsed pulse travel time, compensation can be made for variations in the thickness of the wear member 12 resulting from temperature variations. In addition, through manipulation of the resulting pulse travel time data and calibration as a function of pressure, compensation can be made for variations in the thickness of the wear member 12 resulting from variations in the pressure to which the member 12 is subjected.

The advantage of interposing the piezoelectric element 18 between the reference acoustical member 96 and the portion of the wear member 12 whose thickness is being monitored or measured, and using the piezoelectric element to simultaneously transmit pressure pulses in opposite directions is that signal degradation is minimized and a high signal-to-noise ratio is maintained. For example, if the reference acoustical member is located on the same side of the piezoelectric element as the portion of the wear member whose thickness is being monitored or measured, i.e., the reference acoustical member is interposed between the piezoelectric element and the "monitored or measured" portion of the wear member, pressure pulses only in one direction are required. However, each pressure pulse must pass through the reference acoustical member, the portion of the wear member whose thickness is being monitored or measured, and the interface therebetween. The end result is significant degradation and attenuation of the signal and substantial differences in the amplitude of the "echo" return pulses from the foregoing interface and the inner surface of the wear member. Such signal degradation and differences in pulse amplitude results in inaccuracies in elapsed travel time measurements, low signal-to-noise ratios, and inaccuracies in the "temperature compensations" made for variations in the thickness of the wear member.

As previously indicated, physical properties other than the thickness of, the amount of wear has occurred to, and the amount of material which has been removed from the wear member can be measured and/or monitored by the transducer 10. For example, it has also been found that strain due to stress being applied to the wear member can be readily monitored by one or more transducers mounted within or attached to the wear member. By such monitoring, appropriate means can be taken to minimize and/or control such stress within the wear member. It has also been found that local temperature within the wear member can be determined with one or more transducers and, in the case of rotating equipment, the relative vibration and alignment between the shaft and the wear member can be measured and/or monitored by the transducers. It has been further found that if ball bearings are being utilized, the pressure characteristics of each ball can be measured and/or monitored by a transducer to determine ball wear or fracture.

Figure 7:
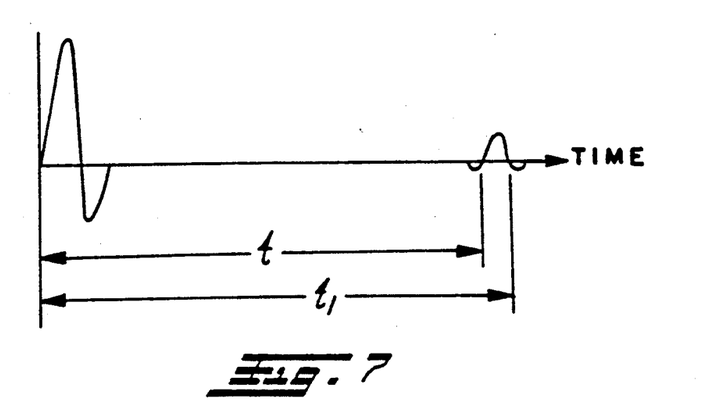
FIG. 7 illustrates an interrogating pulse to and a return "echo" pulse from an ultrasonic piezoelectric transducer embodying the invention of this disclosure.

Another approach for obtaining temperature compensation when using the transducer 10 or for measuring temperature of the wear member 12 with the transducer 10 is shown in FIG. 7 which illustrates an interrogating voltage pulse which is applied to the transducer 10 and the resulting return "echo" voltage pulse produced by the same transducer. The return voltage pulse is defined by a first zero crossing point corresponding to time t and a second zero crossing point corresponding to time $t_1$. It has been found experimentally, that the ratios $t_1/t$, and thus $(t_1-t)/t$, are relatively independent of temperature and pressure variations to which the transducer and the wear member may be subjected and these ratios remain substantially constant unless wear has occurred. Even though the foregoing ratios are relatively independent of temperature and pressure, the time t and the time interval $t_1-t$ are each a function of temperature. Thus, if the temperature of the wear member 12 is initially determined, and time t and the time interval $t_1-t$ are measured at the time of initial temperature determination, a measurement of time t and the time interval $t_1-t$ after a temperature change has occurred to the wear member 12 can be utilized to determine the temperature of the transducer 10 or the wear member 12. Alternatively, the temperature of the wear member 12 can be determined by using a reference transducer 80, as in FIG. 5, and the resulting temperature can be substituted in the functional relationship between temperature, pressure and the time interval $t_1-t$ to determine pressure. Thus, the time t and the time interval $t_1-t$ can be utilized to determine the wear, temperature and/or the pressure to which the transducer and/or wear member are being subjected.

Temperature compensation can also be achieved without the use of a reference acoustical member or a separate reference transducer by incorporating a relative time reference into the transducer. The foregoing is accomplished in the alternate embodiment of the transducer 110 shown in FIG. 8. The structure of this transducer 110 is similar to the transducer 64 shown in FIG. 4 in that it is comprised of an outer sleeve 14, a spacer 16, a piezoelectric element 18, an electrical conductor 50, all of which are received within a blind bore 66 in a wear reference member 68, however, the end 72 of the wear reference member 68 has a centrally located tip 112 protruding therefrom. As in FIG. 4, the wear reference member 68 is received within the through bore 60 in the wear member 12, however, its end 72 is not flush with the inner surface 40 of the wear member 12. The end 72 of the wear reference member 68 forms a plane which is opposite a portion of the piezoelectric element 18 to intercept and reflect a portion of the pressure pulses transmitted thereby. The end 114 of the centrally located tip 112 is machined to ensure that it is flush with the inner surface 40 of the wear member 12 and substantially parallel to the end 72 of the wear reference member 68. In this embodiment, the distance x between the bottom surface 116 of the blind bore 66 and the end 72 of the wear reference member 68 can be accurately measured and acts as a reference distance. Since the end 72 of the wear reference member 68 is not subjected to wear, the distance x is affected only by changes in the temperature of transducer 110. The distance y between the bottom surface 116 of the blind bore 66 and the end 114 of the centrally located tip 112 is subject to change due to wear and variations in transducer temperature.

Figure 8:
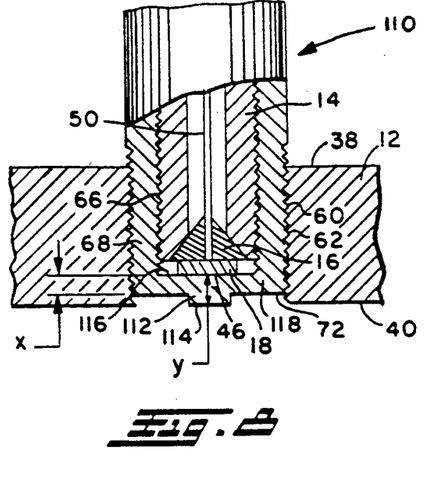
FIG. 8 is a partial cross-sectional view of another embodiment of an ultrasonic piezoelectric transducer installed in a wear member and which provides a relative time reference for temperature compensation.

Operationally, a short voltage pulse is applied to the piezoelectric element 18 via the electrical conductor 50. The piezoelectric element 18 converts the voltage pulse into a pressure pulse (stress pulse) which is transmitted into the bottom portion 118 of the wear reference member 68 via the one side 46 of the element 18. The pressure pulse that is transmitted is reflected by the end 72 of the wear reference member 68 and by the end 114 of the centrally located tip 112 resulting in two "echo" return pressure pulses being transmitted back toward the one side 46 of the piezoelectric element 18 which intercepts same. Appropriate means (not shown) are utilized to separate these two "echo" return pressure pulses. In addition, the elapsed time between the transmission of the initial pressure pulse and the receipt of each of the two "echo" return pressure pulses can be determined. The elapsed time between the transmission of the initial pressure pulse and the receipt of the "echo" return pressure pulse from the end 72 of the wear reference member 68 is representative of distance x which changes with temperature but is unaffected by wear since it is not a wear surface. The elapsed time between the transmission of the initial pressure pulse and the receipt of the "echo" return pressure pulse from the end 114 of centrally located tip 112 is representative of the distance y which changes with temperature and wear since the end 114 of tip 112 is a wear surface. Inasmuch as the temperature of the bottom portion 118 of the wear reference member 68 and the centrally located tip 112 are substantially the same, by comparing the elapsed times between the transmission of the initial pressure pulse and the receipt of each of the two "echo" return pressure pulses, compensation can be made for the operating temperature of the transducer 110 and a very accurate indication of the amount of wear which has occurred to the end 114 of centrally located tip 112 can be determined. In this manner, temperature compensation can be easily accomplished without the use of a reference acoustical member and/or a separate reference transducer.

Figure 9:
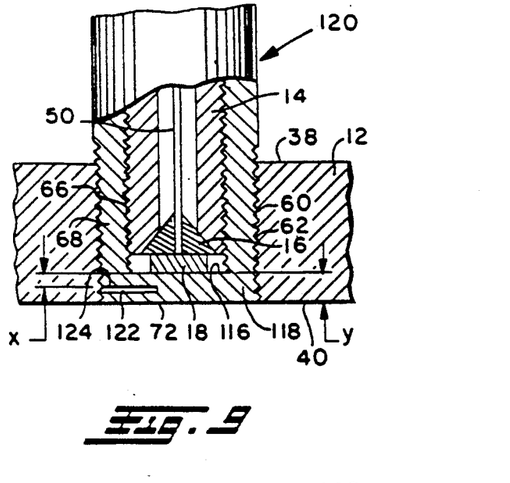
FIG. 9 is a partial cross-sectional view of another embodiment of an ultrasonic piezoelectric transducer installed in a wear member and which provides a relative time reference for temperature compensation.

An alternate embodiment of the transducer 110, shown in FIG. 8, is transducer 120, illustrated in FIG. 9. In this embodiment, those elements which are similar to the elements shown in FIGS. 4 and 8 carry the same reference numerals and will not be discussed further. This transducer 120 differs from transducer 110 in that the wear reference member 68 has a horizontal slot 122 passing partially therethrough. The horizontal slot 122 is substantially parallel to but spaced apart from the end 72 of the wear reference member 68. The top surface 124 of the horizontal slot 122 forms a plane which is opposite a portion of the piezoelectric element 18 to intercept and reflect a portion of the pressure pulses transmitted thereby. This transducer 120 further differs in that the wear reference member 68 does not have a centrally located tip 112. In this case, the distance x (the reference distance) is between the bottom surface 116 of blind bore 66 and the top surface 124 of the slot 122 and the distance y is between bottom surface 116 of blind bore 66 and the end 72 of the wear reference member 68. As in the previous embodiment, a short voltage pulse is applied to the piezoelectric element 18 which converts the voltage into a pressure pulse (stress pulse) which is transmitted into the bottom portion 118 of the wear reference member 68. The foregoing pressure pulse is reflected by the top surface 124 of the slot 122 and the end 72 of the wear reference member 68 resulting in two "echo" return pressure pulses which are separated. By measuring the elapsed times between the transmission of the initial pressure pulse and the receipt of each of the two "echo" return pressure pulses, and by comparing these elapsed times, compensation for temperature can be made so that the wear which has occurred to the end 72 of the wear reference member 68 can be accurately determined.

Figure 10:
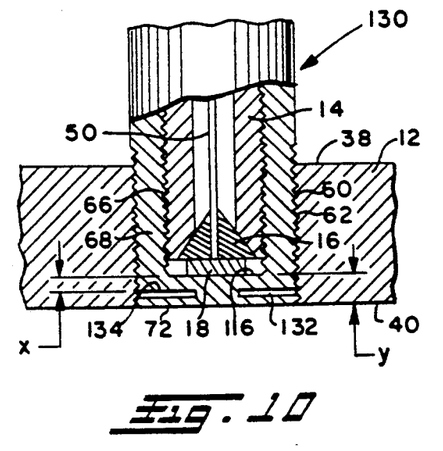
FIG. 10 is a partial cross-sectional view of another embodiment of an ultrasonic piezoelectric transducer installed in a wear member and which provides a relative time reference for temperature compensation.

An alternate embodiment of the transducer 120, shown in FIG. 9, is transducer 130, illustrated in FIG. 10. Here again, those elements which are similar to the elements shown in FIGS. 4, 8 and 9 carry the same reference numerals and will not be discussed further. This transducer 130 differs from transducer 120 in that the horizontal slot 122 is replaced by a circumferential horizontal slot 132 which is substantially parallel to but spaced apart from the end 72 of the wear reference member 68. The top surface 134 of the circumferential horizontal slot 132 forms a plane which is opposite a portion of the piezoelectric element 18 to intercept and reflect a portion of the pressure pulses transmitted thereby. In this case, the distance x (the reference distance) is between the bottom surface 116 of the blind bore 66 and the top surface 134 of the circumferential horizontal slot 132 and the distance y is between the bottom surface 116 of the blind bore 66 and the end 72 of the wear reference member 68. As in the previous embodiments, the top surface 134 of the circumferential horizontal slot 132 and the end 72 of the wear reference member 68 produce separate "echo" return pressure pulses in response to a pressure pulse from the piezoelectric element 18. Similarly, as in the previous embodiments, by measuring and comparing the elapsed times between the transmission of the initial pressure pulse and the receipt of each of the two "echo" return pressure pulses, temperature compensation can be accomplished and an accurate determination of the wear which has occurred to the end 72 of the wear reference member 68 can be made.

Figure 11:
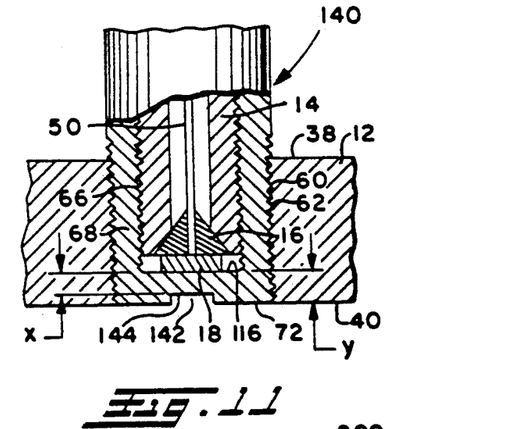
FIG. 11 is a partial cross-sectional view of another embodiment of an ultrasonic piezoelectric transducer installed in a wear member and which provides a relative time reference for temperature compensation.

A still another alternate embodiment of the transducer 110, shown in FIG. 8, is transducer 140, illustrated in FIG. 11. Here again, those elements which are similar to the elements shown in FIG. 8 carry the same reference numerals and will not be discussed further. This transducer 140 differs from transducer 110 in that the centrally located tip 112 on transducer 110 is replaced by a centrally located recess 142. The top surface 144 of the centrally located recess 142 is substantially parallel to the end 72 of the wear reference member 68 and forms a plane which is opposite a portion of the piezoelectric element 18 to intercept and reflect a portion of the pressure pulses transmitted thereby. In this case, the distance x (the reference difference) is between the bottom surface 116 of the blind bore 66 and the top surface 144 of the centrally located recess 142 and the distance y is similar to that in FIGS. 9 and 10 since it is from the bottom surface 116 of the blind bore 66 to the end 72 of the wear reference member 68. As in all of the previous embodiments, the transmission of a pressure pulse by the piezoelectric element 18 results in two "echo" return pressure pulses, one "echo" return pulse from the top surface 144 of the centrally located recess 142 and the other "echo" return pressure pulse from the end 72 of the wear reference member 68. By measuring and comparing the elapsed times between the transmission of the initial pressure pulse and the receipt of each of the two "echo" return pressure pulses, compensation can be made for temperature so that the wear which has occurred to the end 72 of the wear reference member 68 can be accurately determined.

Figure 12:
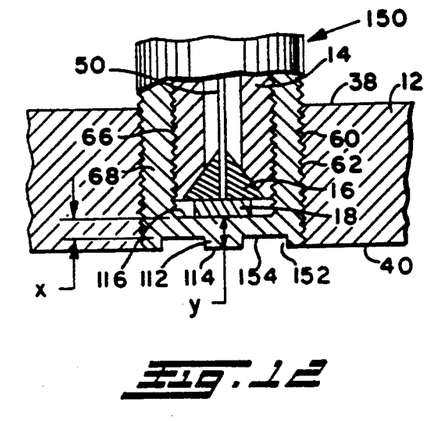
FIG. 12 is a partial cross-sectional view of another embodiment of an ultrasonic piezoelectric transducer installed in a wear member and which provides a relative time reference for temperature compensation.

Another alternate embodiment of transducer 110, shown in FIG. 8, is transducer 150, illustrated in FIG. 12. As in the all of the previous embodiments, those elements which are similar to the elements shown in FIG. 8 carry the same reference numerals and will not be discussed further. The transducer 150 differs from transducer 110 in that the end 72 of the wear reference member 68 has a circumferential pocket 152 formed therein with the tip 112 protruding substantially centrally therefrom. The top surface 154 of the circumferential pocket 152 is substantially parallel to the end 114 of the centrally located tip 112 and forms a plane which is opposite a portion of the piezoelectric element 18 to intercept and reflect a portion of the pressure pulses transmitted thereby. In this case, the distance x (the reference distance) is between the bottom surface 116 of the blind bore 66 and the top surface 154 of the circumferential pocket 152. The distance y is the same as in FIG. 8 in that it is from the bottom surface 116 of blind bore 66 to the end 114 of the centrally located tip 112. As in all of the other previous embodiments, the transmission of a pressure pulse (stress pulse) by the piezoelectric element 18 into the bottom portion 118 of the wear reference member 68 causes two "echo" return pressure pulses to be formed—one "echo" return pressure pulse being reflected by the top surface 154 of the circumferential pocket 152 and the other "echo" return pressure pulse being reflected from the end 114 of the centrally located tip 112. Here again, by measuring the elapsed times between the transmission of the initial pressure pulse and the receipt of each of the two "echo" return pressure pulses, and by comparing these elapsed times, temperature compensation can be accomplished and an accurate determination of the wear which has occurred to the end 114 of the centrally located tip 112 can be made.

Figure 13:
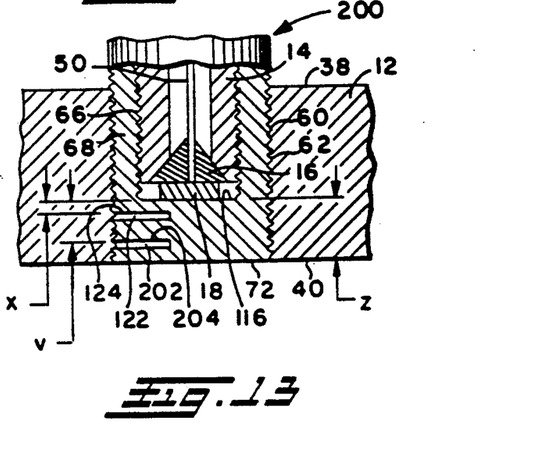
FIG. 13 is a partial cross-sectional view of another embodiment of an ultrasonic piezoelectric transducer installed in a wear member and which provides a plurality of relative time references for temperature compensation.

An alternate embodiment of the transducer 120, shown in FIG. 9, is transducer 200, illustrated in FIG. 13. In this embodiment, those elements which are similar to the elements shown in FIGS. 4 and 9 carry the same reference numerals and will not be discussed further. This transducer 200 differs from transducer 120 in that the wear reference member 68 has an additional horizontal slot 202 provided therein. The horizontal slot 202 is substantially parallel to horizontal slot 122 but is spaced apart therefrom. In addition, the horizontal slot 202 is substantially parallel to and spaced apart from the end 72 of the wear reference member 68. The horizontal slot 202 can be placed on the same side of wear reference member 68 as slot 122 or can be offset therefrom; the only requirement being that the horizontal slot 202 is substantially parallel to the horizontal slot 122 and to the end 72 of the wear reference member 68. In addition, the width and depth of the horizontal slot 202 can be the same as or different from the respective width and depth of the horizontal slot 122. The top surfaces 124 and 204 of the horizontal slots 122 and 202, respectively, form planes which are opposite a portion of the piezoelectric element 18 to intercept and reflect a portion of the pressure pulses transmitted thereby. In this case, the distance x (the first reference distance) is between the bottom surface 116 of the blind bore 66 and the top surface 124 of the slot 22; the distance y (the second reference distance) is between the bottom surface 116 of the blind bore 66 and the top surface 204 of the slot 202; and the distance z is between the bottom surface 116 of the blind bore 66 and the end 72 of the wear reference member 68.

Operationally, a short voltage pulse is applied to the piezoelectric element 18 via the electrical conductor 50. The piezoelectric element 18 converts the voltage pulse into a pressure pulse (stress pulse) which is transmitted into the bottom portion 118 of the wear reference member 68 via the one side 46 of the element 18. The foregoing pressure pulse is reflected by the top surface 124 of the slot 122, by the top surface 204 of the slot 202 and by the end 72 of the wear reference member 68 resulting in three "echo" return pressure pulses being transmitted back toward the one side 46 of the piezoelectric element which intercepts same. Appropriate means (not shown) are utilized to separate these three "echo" return pressure pulses. In addition, the elapsed time between the transmission of the initial pressure pulse and the receipt of each of the three "echo" return pressure pulses can be determined. By measuring the elapsed times between the transmission of the initial pressure pulse and the receipt of each of the three "echo" return pressure pulses, and by comparing these elapsed times, the temperature gradient which exists between the bottom surface 116 of the blind bore 66 and the end 72 of the wear reference member 68 or between the bottom surface 116 of the blind bore 66 and each of the slots 122 and 202, or between each of the foregoing slots 122 and 202, or between each of the foregoing slots 122 and 202 and the end 72 of the wear reference member 68 can be determined. With the use of the foregoing determinations, compensation for temperature can be made so that the wear which has occurred to the end 72 of the wear reference member 68 can be accurately determined, and through interpolation and extrapolation techniques, the temperature of the surface defining the end 72 can be determined with a very high degree of accuracy. Thus, remote sensing of the temperature of the wear surface can be effected without the use of a temperature sensing device, such as a thermocouple.

It should be noted that the foregoing embodiments of transducers (FIGS. 8 through 13) and the waveform illustrated in FIG. 7 show that temperature compensation can be readily achieved without the use of a reference acoustical member, such as an interposing buffer or a separate reference transducer. It should be further noted that the foregoing structures shown in these Figures illustrate typical structures, and many other structures are obtainable and can be used to achieve the same result. Thus, the structures are representative structures and, in no way, illustrate all of the structures which can be produced to obtain a transducer in which temperature compensation can be achieved without the use of a reference acoustical member or a separate reference transducer. Regardless of the structure utilized, the objective is to provide a relative time reference surface as close as possible to the wear member surface being monitored so that wear can be accurately determined.

It has been found that transducer 140, illustrated in FIG. 11, and possibly some of the other transducers described herein, can be utilized to determine the position of a rotating shaft relative to a non-wear surface, e.g., the top surface 144 of recess 142. In this case, the pressure pulse transmitted by the piezoelectric element 18 will "jump the gap" between the top surface 144 of recess 142 and the surface of the shaft resulting in an additional "echo" return pressure pulse from the surface of the shaft. By comparing the additional "echo" return pressure pulse with the foregoing two "echo" return pressure pulses, the position of the shaft relative to the end 72 of the wear reference member 68 and the thickness of the oil film therebetween can be determined. It has been found experimentally that oil film thickness of less than 0.002 in. to more than 0.040 in. can be measured.

Figure 14:
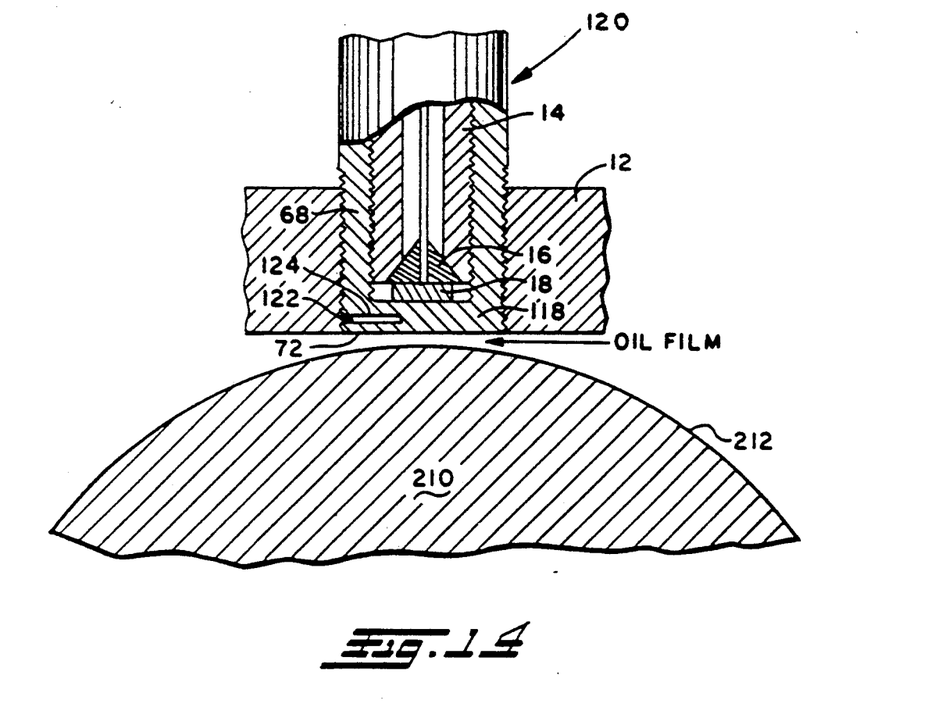
FIG. 14 is a partial cross-sectional view of a piezoelectric ultrasonic transducer, similar to the transducer shown in FIG. 9, installed in a wear member and illustrates the position of the transducer relative to a rotating shaft.
Figure 15:
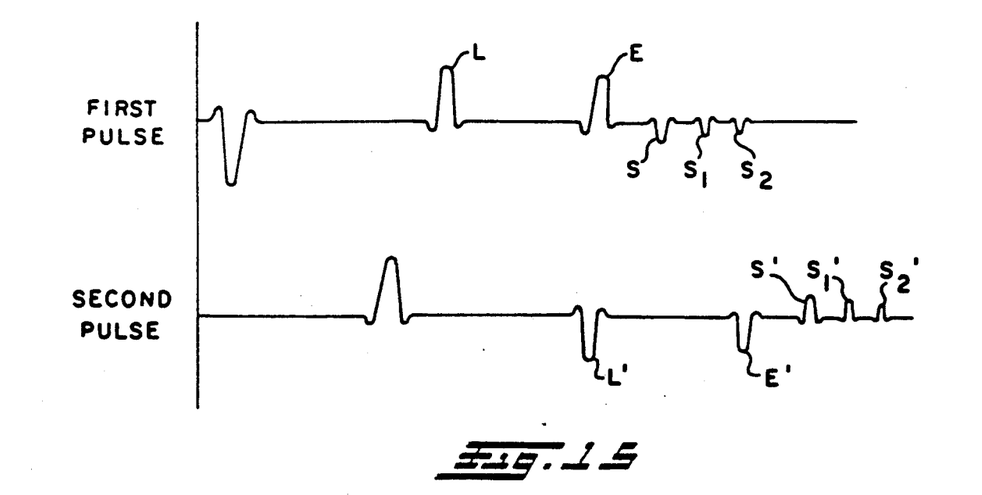
FIG. 15 illustrates a first pressure pulse and a second pressure pulse having an opposite polarity, said pressure pulses being produced by the piezoelectric element within the transducer shown in FIG. 14, and shows the respective "echo" return pressure pulses from a slot within the transducer, the end of the transducer, and the surface of the rotating shaft.

Another approach for "jumping the gap" between the end 72 of the wear reference member 68 and the surface of a shaft is illustrated in FIGS. 14 and 15. FIG. 14 illustrates the transducer 120, as shown in FIG. 9, mounted so as to be in close proximity to a shaft 210. In this case, the pressure pulse (stress pulse) produced by the piezoelectric element 18 is transmitted into the bottom portion 118 of the wear reference member 68. The foregoing pressure pulse is reflected by the top surface 124 of the slot 122, the end 72 of the wear reference member 68 and the surface 212 of the shaft 210 resulting in a waveform that has three distinct "echo" return pressure pulses which are separated from one another with respect to time. In addition, multiple "echo" return pressure pulses of a smaller magnitude are produced as the "echo" return pressure pulse from the surface 212 of the shaft 210 is reflected back and forth between the surface 212 of the shaft 210 and the end 72 of the wear reference member 68. The foregoing "echo" return pressure pulses are illustrated in FIG. 15 and designated as pulses L, E and S from surface 124 of the slot 122, end 72 of the wear reference member 68 and surface 212 of the shaft 210, respectively. Multiple pressure pulses $S_1$, $S_2$, etc. resulting from the "echo" return pressure pulse S from the surface 212 of the shaft 210 being reflected back and forth between the surface 212 and the end 72 of the wear reference member 68 are also illustrated. In order to effectively "jump the gap" and monitor the position of the shaft 210, such position being represented by pulse S from the surface 212 of shaft 210, pulse E should be made to effectively vanish, i.e., it should be cancelled, due to its close proximity to pulse S in the resulting waveform. Cancellation or subtraction of pulse E can be accomplished by having the piezoelectric element 18 produce a pressure pulse (stress pulse) of a polarity opposite to that which was originally produced and to transmit this pressure pulse of opposite polarity into the bottom portion 118 of the wear reference member 68 resulting in the production of "echo" return pressure pulses L', E' and S' from surface 124 of slot 122, end 72 of wear reference member 68 and surface 212 of shaft 210, respectively. Multiple pressure pulses $S_1$, $S_2$, etc. resulting from the "echo" return pressure pulse S' being reflected back and forth between the surface 212 of the shaft 210 and the end 72 of the wear reference member 68 are similarly illustrated. The timing of the transmission and the amplitude of the pressure pulse of opposite polarity into the bottom portion 118 of the wear reference member 68 can be adjusted so that "echo" return pressure pulse E from the end 72 of the wear reference member 68 is "cancelled" by the "echo" return pressure pulse L' from the surface 124 of the slot 122. In this manner, the only remaining "echo" return pressure pulses will be pulse L from surface 124 of slot 122, pulses S, $S_1$, $S_2$, etc. and S', $S_1$, $S_2$, etc. from surface 212 of shaft 210 and pulse E' from end 72 of wear reference member 68. By determining the elapsed time between "echo" return pressure pulses L and S, the position of the shaft 210 with respect to the slot 122 in the wear reference member 68 can be determined very accurately. In this way, the orbit of the shaft 210 can be monitored continuously even when the oil film between the wear reference member 68 and the shaft 210 is very thin.

Another approach for cancelling "echo" return pressure pulse E involves having the piezoelectric element 18 produce a pressure pulse (stress pulse), transmitting the foregoing pressure pulse into the bottom portion 118 of the wear reference member 68, receiving the "echo" return pressure pulse L from surface 124 of the slot 122, inverting "echo" return pressure pulse L, delaying the inverted "echo" return pressure pulse L, and then adding the delayed inverted "echo" return pressure pulse L to "echo" return pressure pulse E to cancel same. A still another approach involves transmitting a pressure pulse into the bottom portion 118 of the wear reference member 68 when a shaft is not present, receiving the "echo" return pressure pulse E from the end 72 of the wear reference member 68, inverting the pulse E and storing it in memory, and then adding the inverted "echo return pressure pulse E to the "echo" return pressure pulse E when the shaft is present to cancel this latter pressure pulse. Alternatively, with the shaft present and by using digital methods the "echo" return pressure pulse E can be placed in memory and then subtracted from itself to effectively cancel same.

Figure 16:
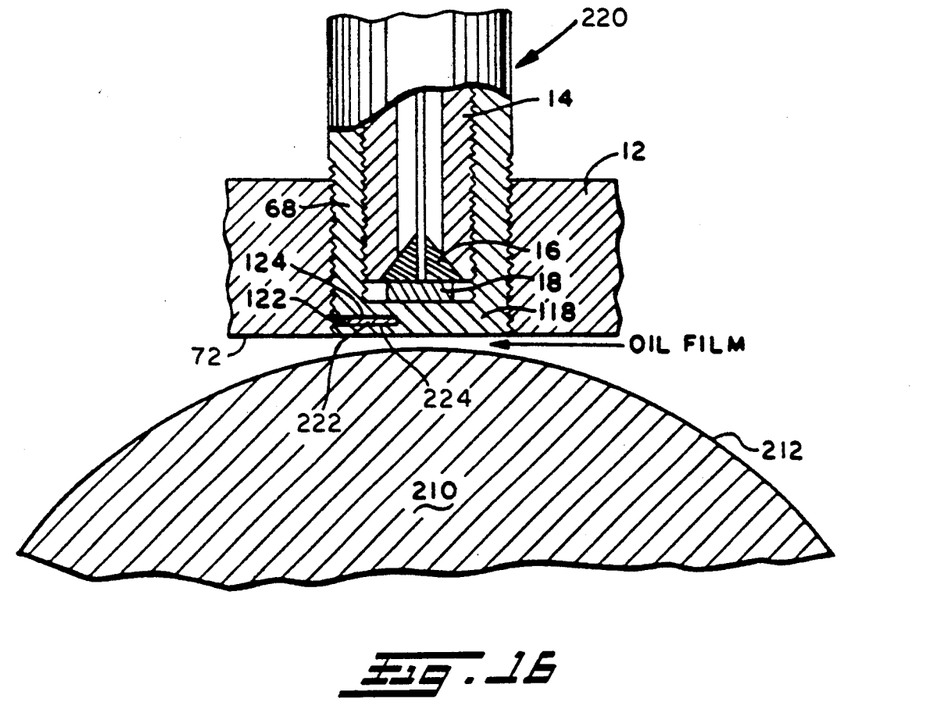
FIG. 16 is a partial cross-sectional view of another embodiment of an ultrasonic piezoelectric transducer, similar to the transducer shown in FIG. 9, installed in a wear member and illustrates the position of the transducer relative to a rotating shaft.
Figure 17:
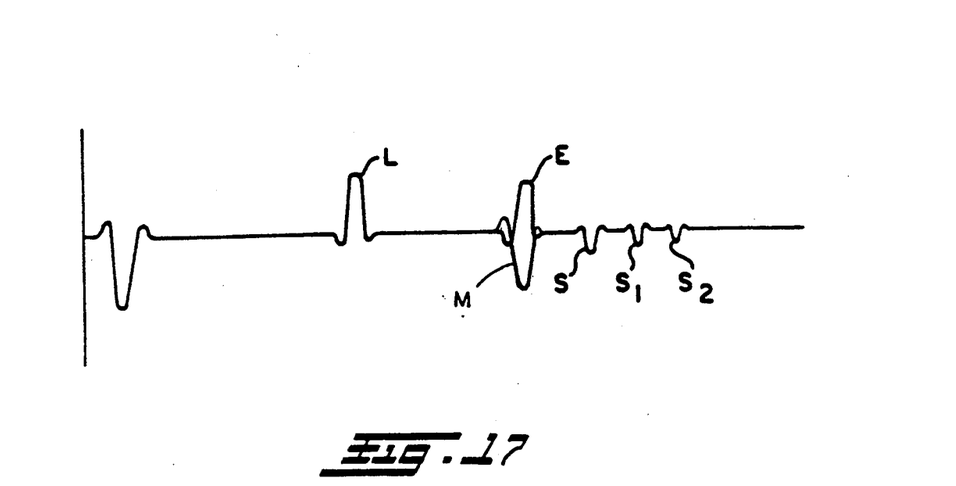
FIG. 17 illustrates a pressure pulse produced by the piezoelectric element within the transducer shown in FIG. 16, and shows the respective "echo" return pressure pulses from the top surface of a slot within the transducer, the bottom surface of the slot, the end of the transducer, and the surface of the rotating shaft.

The transducer can also be designed so as to "mechanically" cancel the "echo" return pressure pulse from the end of the wear reference member. FIG. 16 illustrates a transducer 220 which can "mechanically" cancel the foregoing pressure pulse. Those elements of transducer 220, which is an alternate embodiment of FIG. 9, that are similar to the elements shown in FIG. 9 carry the same reference numerals and will not be discussed further. Transducer 220 differs from transducer 120 in that horizontal slot 122 is filled with an acoustically conducting material 222 that differs from the material comprising the wear reference member 68. In this manner, a first "echo" return pressure pulse is received from the top surface 124 of the slot 122 and a second "echo" return pressure pulse from the bottom surface 224 of the slot 122. The material 222 which fills slot 122 should have an acoustic velocity that is lower than the acoustic velocity of the material comprising the wear reference member 68. By selecting a material having a lower acoustic velocity and by utilizing the parameters that define same, the "echo" return pressure pulse from bottom surface 224 of slot 122 can effectively cancel the "echo" return pressure pulse from the end 72 of the wear reference member 68. Operationally, the pressure pulse (stress pulse) produced by the piezoelectric element 18 is transmitted into the bottom portion 118 of the wear reference member 68. The foregoing pressure pulse is reflected by the top surface 124 of the slot 122, the bottom surface 224 of the slot 122, the end 72 of the wear reference member 68 and the surface 212 of the shaft 210 resulting in a waveform that has four distinct "echo" return pressure pulses that are separated from one another with respect to time. The foregoing "echo" return pressure pulses are illustrated in FIG. 17 and designated as pulses L, M, E and S from top surface 124 of the slot 122, bottom surface 224 of the slot 122, end 72 of the wear reference member 68 and surface 212 of the shaft 210, respectively. In order to effectively "jump the gap" and monitor the position of the shaft 210, such position being represented by pulse S from the surface 212 of the shaft 210, pulse E should be cancelled because of its close proximity to pulse S in the resulting waveform. Cancellation of pulse E can be accomplished by varying the distance between the top surface 124 and the bottom surface 224 of the slot 122 and/or the type of material 222 used therein so that pulse M from the bottom surface 224 of the slot 122 substantially coincides, in time, with pulse E from the end 72 of the wear reference member 68. Since pulse M from the bottom surface 224 of slot 122 is of opposite polarity to pulse E from the end 72 of the wear reference member 68, pulse E is effectively cancelled, thus permitting an accurate measurement of pulse S from surface 212 of the shaft 210. By determining the elapsed time between "echo" return pressure pulses L and S, the position of the shaft 210 with respect to wear reference member 68 can be determined very accurately. In this manner, the orbit of the shaft 210 can be monitored continuously even when the oil film between the wear reference member 68 and the shaft 210 is very thin.

Thus, it is apparent that the position of the shaft 210 and/or the thickness of the oil film between end of the wear reference member 68 and the shaft 210 can be readily determined electrically or mechanically.

The foregoing illustrations of methods or approaches for "cancelling" the "echo" return pressure pulse E in order to monitor the position of the shaft 210 should not be considered to be the only approaches to effectively cancel this pulse, but merely illustrate some of the approaches that can be utilized. Other approaches are available to accomplish the same result, viz., the cancellation of "echo" return pressure pulse E.

Certain modifications and improvements will occur to those skilled in the art upon reading the foregoing. It should be understood that all such modifications and improvements have been deleted herein for the sake of conciseness and readability, but are properly within the scope of the following claims.

We claim:

1. An ultrasonic transducer device for measuring the thickness of a member comprising a piezoelectric element, means for biasing said piezoelectric element against the member whose thickness is to be measured, said biasing means comprising a sleeve having a recess provided in one end thereof and spacer means received within said recess in said sleeve, said spacer means operatively contacting said piezoelectric element, and means for producing a plurality of reference thicknesses, said reference thickness producing means being received within the member whose thickness is to be measured and being formed from a material having an acoustical velocity differing from the acoustic velocity of the member whose thickness is to be measured, said reference thickness producing means and a wear surface on said member intercepting signals produced by said piezoelectric element in response to actuation thereof and producing return signals differing in time relative to one another.

2. The transducer device as defined in claim 1 wherein the acoustic velocity of said material comprising said reference thickness producing means is less than the acoustic velocity of the member whose thickness is to be measured.

3. The transducer device as defined in claim 1 wherein at least one of the surfaces defining said reference thickness producing means is substantially parallel to said wear surface on the member whose thickness is to be measured.

4. The transducer device as defined in claim 1 wherein said piezoelectric element has a pair of faces, one of said pair of faces being in operative engagement with a surface of the member whose thickness is to be measured and with said reference thickness producing means, the other of said pair of faces being contacted by said biasing means.

5. An ultrasonic transducer device for measuring the thickness of a member comprising, in combination, a piezoelectric element, a member whose thickness is to be measured, means for biasing said piezoelectric element against said member whose thickness is to be measured, said biasing means comprising a sleeve having a recess provided in one end thereof and spacer means received within said recess in said sleeve, said spacer means operatively contacting said piezoelectric element, and means for producing a plurality of reference thicknesses, said reference thickness producing means being received within said member whose thickness is to be measured and being formed from a material having an acoustic velocity that differs from the acoustic velocity of said member whose thickness is to be measured, said reference thickness producing means and a wear surface on said member intercepting signals produced by said piezoelectric element in response to actuation thereof and producing return signals differing in time relative to one another.

6. The combination as defined in claim 5 wherein the acoustic velocity of said material comprising said reference thickness producing means is less than the acoustic velocity of said member whose thickness is to be measured.

7. The combination as defined in claim 5 wherein at least one of the surfaces defining said reference thickness producing means is substantially parallel to said wear surface on said member whose thickness is to be measured.

8. The combination as defined in claim 5 wherein said piezoelectric element has a pair of faces, one of said pair of faces being in operative engagement with a surface of said member whose thickness is to be measured and with said reference thickness producing means, the other of said pair of faces being contacted by said biasing means.

9. A method for measuring the thickness of a member in-situ through the use of an ultrasonic transducer device comprising a piezoelectric element, means for biasing said piezoelectric element against the member whose thickness is to be measured, said biasing means comprising a sleeve having a recess provided in one end thereof and spacer means received within said recess in said sleeve, said spacer means operatively contacting said piezoelectric element, and means for producing a plurality of reference thicknesses, said reference thickness producing means being formed from a material having an acoustic velocity that differs from the acoustic velocity of the member whose thickness is to be measured, said method comprising the steps of:
   applying a pulse to said ultrasonic transducer device causing said piezoelectric element to transmit an interrogating signal into the member whose thickness is to be measured;
   receiving a return signal from at least one of the surfaces defining said reference thickness producing means and from the end of the member whose thickness is to be measured in response to said interrogating signal;
   processing said return signals to eliminate the effects thereon of any temperature gradients which exist in the member whose thickness is to be measured; and
   determining the thickness of the member from said processed return signals.

10. The method as defined in claim 9 wherein the acoustic velocity of each material comprising said reference thickness producing means is less than the acoustic velocity of the member whose thickness is to be measured.

11. A method for determining the position of a member through the use of an ultrasonic transducer device comprising a piezoelectric element, a reference member, means for biasing said piezoelectric element against a surface of said reference member, said biasing means comprising a sleeve having a recess provided in one end thereof and spacer means received within said recess in said sleeve, said spacer means operatively contacting said piezoelectric element, and means for producing a plurality of reference thicknesses, said reference thickness producing means being formed from material having an acoustic velocity that differs from the acoustic velocity of said reference member, said method comprising the steps of:

locating said ultrasonic transducer device in proximity to the member whose position is to be determined;

applying a pulse to said ultrasonic transducer device causing said piezoelectric element to transmit an interrogating signal into said reference member and into the member whose position is to be determined;

receiving a return signal from at least one of the surfaces defining said reference thickness producing means and from the end of said reference member and from the member whose position is to be determined;

processing said return signals to eliminate the return signal produced from said end of said reference member; and determining the position of the member from said processed return signals.

12. The method as defined in claim 11 wherein the acoustic velocity of said material comprising said reference thickness producing means is less than the acoustic velocity of said reference member.

* * * * *